(12) United States Patent
Sakai

(10) Patent No.: US 6,186,975 B1
(45) Date of Patent: Feb. 13, 2001

(54) LIQUID CONVEYING CATHETER

(75) Inventor: Toshinori Sakai, Shizuoka (JP)

(73) Assignee: Suzuki Motor Corporation, Shizuoka (JP)

( * ) Notice: Under 35 U.S.C. 154(b), the term of this patent shall be extended for 0 days.

(21) Appl. No.: 09/430,183

(22) Filed: Oct. 29, 1999

(30) Foreign Application Priority Data

Oct. 30, 1998 (JP) .................................................. 10-309625

(51) Int. Cl.[7] ..................................................... A61M 1/00

(52) U.S. Cl. ............................................ 604/35; 604/902

(58) Field of Search .............................. 604/35, 264, 28, 604/30, 523, 902

(56) References Cited

U.S. PATENT DOCUMENTS

| 5,217,465 | * | 6/1993 | Steppe .................................. 604/35 X |
| 5,271,735 | * | 12/1993 | Greenfield et al. ................. 604/35 X |
| 5,310,406 | * | 5/1994 | Sharpe et al. ........................... 604/35 |
| 5,785,678 | * | 7/1998 | Griep et al. .............................. 604/28 |

\* cited by examiner

*Primary Examiner*—John D. Yasko
(74) *Attorney, Agent, or Firm*—Greenblum & Bernstein, P.L.C.

(57) ABSTRACT

The present invention provides a liquid conveying catheter comprising a collecting tube inserted into an object for sucking a liquid from its tip, a mixing bar extending through the collecting tube, and a drive unit for rotating the mixing bar. The collecting tube has on its inner wall a helical convex to define a helical groove serving as a flow path.

20 Claims, 8 Drawing Sheets

LIQUID CONVEYING CATHETER

BACKGROUND OF THE INVENTION

1. Field of the Invention

The present invention relates to a liquid conveying catheter and in particular, to a liquid conveying catheter for introducing a predetermined liquid into a living body and collecting a liquid from the living body.

2. Description of the Related Art

Conventionally, in the medical field, catheters have been used for inspection and curing. Currently, the catheters are used for the respiration organ, digestion organ, circulatory organ, and other organs.

FIG. 8 shows a conventional liquid conveying catheter 100 comprising a liquid supply tube 101 for introducing a predetermined liquid into a living body and a liquid collecting tube 102 for collecting a surplus portion of the liquid. An insert end of the liquid supply tube 101 and an insert end of the liquid collecting tube 102 are combined together for insertion. The other end of the liquid supply tube 101 is connected to a liquid reservoir (not depicted) and a positive pressure pump 103 for feeding the liquid to the insert end. The other end of the liquid collecting tube 102 is connected to a negative pressure pump 104.

The insert end of the liquid supply tube 101 and the insert end of the liquid collecting tube 102 are inserted into a living body. A liquid is supplied via the liquid supply tube 101 by the positive pressure pump 103, and a surplus liquid is collected via the liquid collecting tube 102 by the negative pressure pump 104.

Here, the liquid collecting tube 102 is often collapsed by a negative pressure, depending on the material constituting the liquid collecting tube 102, disabling liquid flow in the liquid collecting tube 102.

SUMMARY OF THE INVENTION

It is therefore an object of the present invention to provide a liquid conveying catheter capable of collecting a liquid at a constant rate while making the insert end very small.

The liquid conveying catheter according to the present invention is for conveying a liquid from an object from which a liquid is to be collected, the catheter comprising: a collecting tube having an insert end inserted into the object for sucking a liquid; a mixing bar extending through the collecting tube and rotatably supported; and a drive unit for rotating the mixing bar, wherein the collecting tube has a helical convex on its inner wall around the center axis of the collecting tube, so as to define a helical groove.

In this configuration, the tip end of the collecting pipe is inserted into the object to/from which a liquid is carried, and a predetermined liquid is sucked from the tip end of the collecting pipe.

For suction, a collected liquid is urged to rotate along the helical groove by the mixing bar driven by a drive unit.

Even if the collecting tube is curved or cross sectional area is reduced, the mixing bar is brought into abutment with the helical convex, preventing further deformation of the collecting tube. Thus, the liquid is sucked at a constant rate.

The aforementioned configuration may include a supply tube whose insert end is inserted into the object for discharging a liquid into the object. For example, such a configuration is provided together with an observation unit such as an image fiber unit. When the tubes are inserted into a blood vessel, the supply unit discharges a physiological saline solution as a predetermined liquid to prevent the image fiber from being covered with blood, thus assuring a field of view, while a surplus physiological saline solution is collected together with blood by the collecting tube.

This supply tube is inserted into the object simultaneously with the collecting tube. The physiological saline solution is discharged from the insert end of the supply tube while surplus physiological saline solution and blood are collected by the collecting tube.

In this configuration, the helical convex may be formed by a coil-shaped member fixed to the inner surface of the collecting tube. Here, the coil-shaped member may protrude from the insert end of the collecting tube in the insert direction. This protrusion serves as a filter for preventing a solid piece from being introduced in the collecting tube, which may cause clogging of the tube.

Moreover, instead of protruding the coil-shaped member, it is also possible to provide a number of through holes at the insert end portion of the collecting tube. This also functions in the same way.

Furthermore, the mixing bar preferably has an elliptical cross section. In this case, the liquid in the rotary radius of the mixing bar is directly urged to rotate, increasing the flow rate.

Alternatively, the mixing bar may have a circular cross section and have a helical convex on the outer circumferential surface so as to define a helical groove. Even if the collecting tube is curved or the cross section area is reduced due to lowering of the inner pressure, the helical groove assures a flow path. Thus, it is possible to obtain an increased flow rate. Furthermore, the helical convex urges the liquid to flow.

Moreover, in the configuration including the collecting tube and the supply tube, the supply tube may also have a helical convex and a mixing bar rotated by a drive unit in the same way as in the collecting tube. In such a configuration, it is possible to obtain a preferable flow even if the liquid supply pressure is increased.

It is also possible to provide a suction pump at the end of the collecting tube. This facilitates liquid suction from the collecting pipe.

DESCRIPTION OF THE PREFERRED EMBODIMENTS

Figure 1:
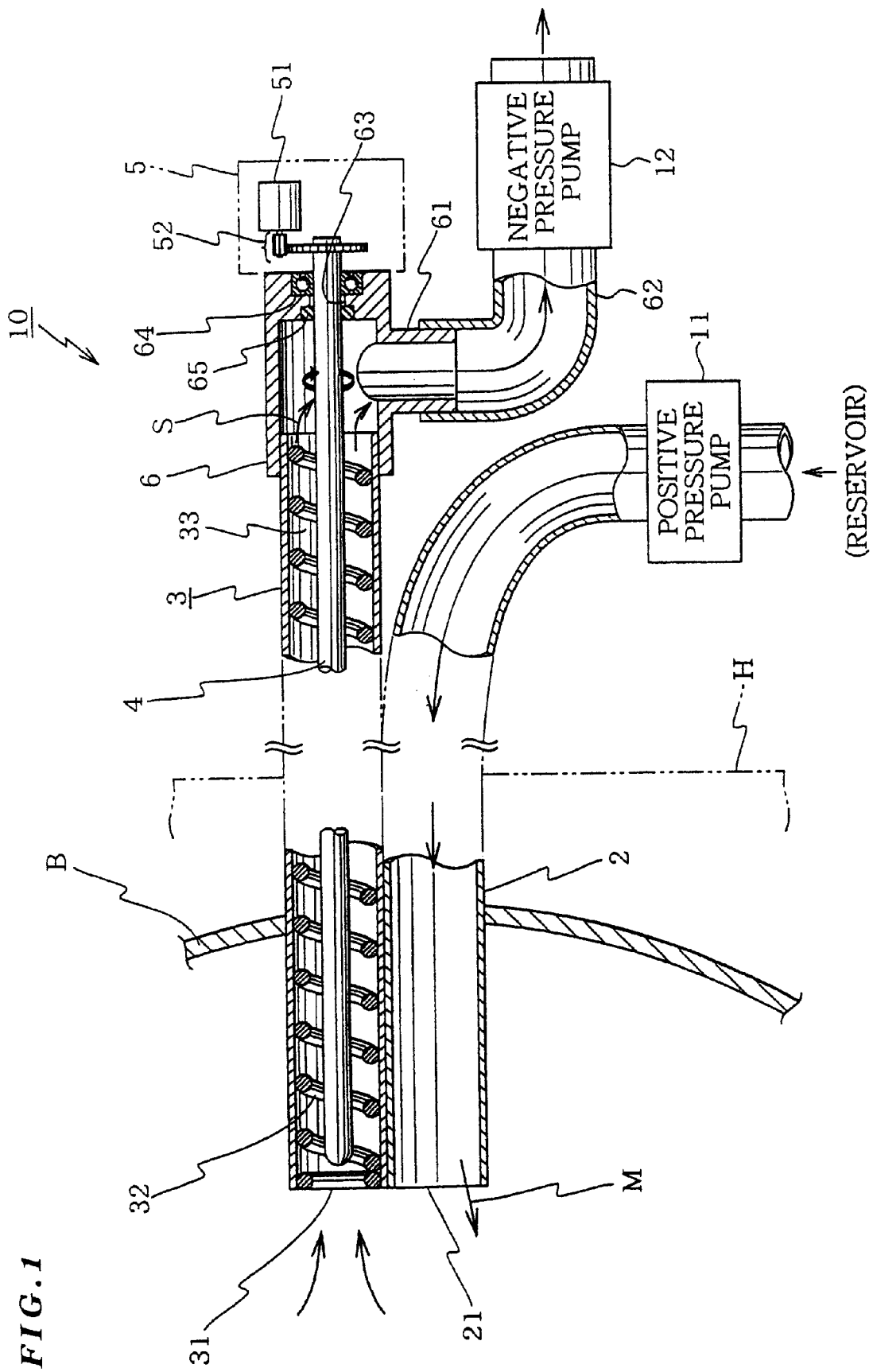
FIG. 1 is a front view of an embodiment of the present invention, partially cut away.
Figure 2:
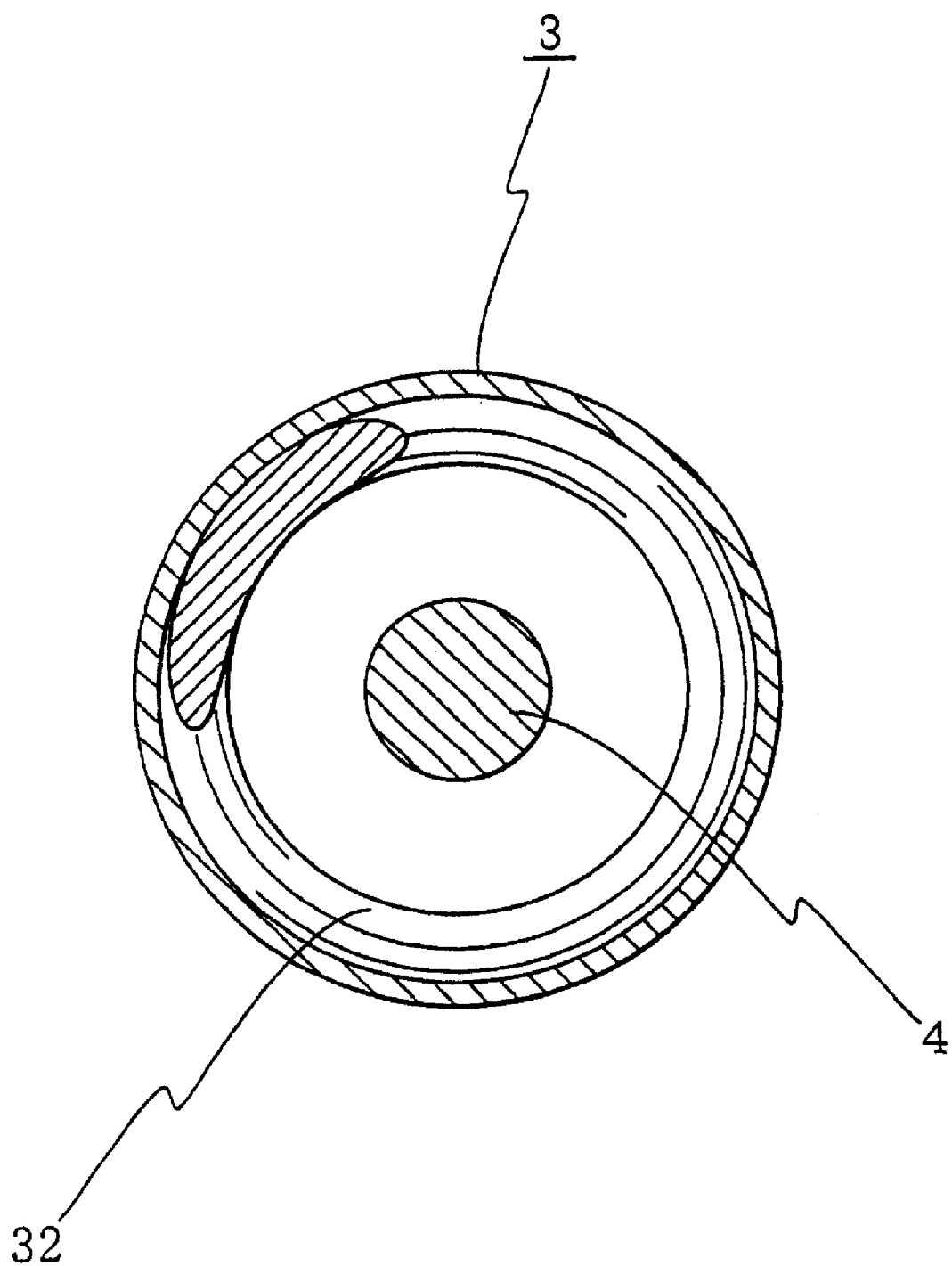
FIG. 2 is a cross sectional view of a collecting tube viewed from the opposite of the suction direction.

Description will now be directed to a liquid conveying catheter according to an embodiment of the present invention with reference to FIG. 1 and FIG. 2.

This catheter 10, for example, can be used together with an image fiber unit for video observation. When they are simultaneously inserted into an organ (such as a blood vessel B) of a living body H, in order to prevent image fiber unit end portion from being covered with blood B, a physiological saline solution M is discharged to secure a field of view, while waste liquid (surplus physiological saline solution and blood) is collected.

FIG. 1 shows this liquid conveying catheter 10 inserted into a blood vessel B of a living body H (image fiber unit is not depicted).

This liquid conveying catheter 10 includes: a supply tube 2 for discharging a physiological saline solution from its insert end 21; a collecting tube 3 inserted together with the supply tube 2 for sucking a liquid from its insert end 31; a mixing bar 4 rotatably arranged in the collecting tube 3; and drive unit 5 for driving to rotate the mixing bar 4.

Each of the components will be detailed below.

Firstly, the supply tube 2 a flexible tube having length of about 1 m and outer diameter in the order of 0.3 mm. The supply tube 2 has a supply end 21 open and a rear end connected via a positive pressure pump 11 to a reservoir of physiological saline solution (not depicted). The positive pressure pump 11 drives the physiological saline solution from the reservoir into the supply tube 2 and is discharged from the supply end 21.

Next, the collecting tube 3 is also a flexible tube, having length of about 1 m and outer diameter in the order of 0.3 mm. This collecting tube 3 is arranged adjacent to the supply tube 2 and has an insert end 31 combined with the supply end 21 of the supply tube 2. As has been described above, since both of the supply tube 2 and the collecting tube 3 have flexibility, after inserted into the blood vessel B, it is possible to move the end portions 21 and 31 to a target position along the blood vessel B.

Moreover, this collecting tube 3 has the insert end 31 which is open and the rear end connected via a buffer member 6 to a negative pressure pump (suction pump) 12. When this negative pressure pump 12 is driven, surplus physiological saline solution M and blood and the like (waste liquid S) are sucked into the collecting tube 3 and exhausted outside via the negative pressure pump 12.

Furthermore, the collecting tube 3 has a helical convex formed on its inner wall centering at the center axis of the collecting tube 3. This helical convex is a coil-shaped member attached to the inner wall of the collecting tube 3. The coil-shaped member has its outer diameter almost identical to the inner wall of the collecting tube 3 and made from the same material as the collecting tube 3. The coil-shaped member is fixed on the inner wall through melting. This coil-shaped member 32 increases the strength in the radial direction without deteriorating the flexibility. Moreover, this coil-shaped member forms a flow path for the waste liquid S.

The buffer member 6 is a bottomed cylindrical member having an inner diameter identical to the outer diameter of the collecting tube 3. The rear end of the collecting tube 3 is covered with this buffer member 6. The buffer member 6 has an exhaust opening 61 on its side surface, which is connected via a hose 62 to the negative pressure pump 12. That is, the waste liquid S flowing from the collecting tube 3 passes through this exhaust opening 62 and discharged by the negative pressure pump 12.

The bottom of the buffer member 6 has a through hole 63, through which the mixing bar 4 is rotatably supported via a bearing 64. Moreover, this through hole has packing 65 so that no waste liquid S can leak.

The mixing bar 4 is positioned at the center of the collecting tube 3 and supported by the buffer member 6. Moreover, the mixing bar 4 has almost identical length as the collecting tube 3 and a circular cross sectional view as shown in FIG. 2. The mixing bar 4 has an outer diameter slightly smaller than the inner diameter of the coil-shaped member 32, so that it can move inside the coil-shaped member 32. This mixing bar 4 also has flexibility and is deflected according to the deflection of the collecting tube 3.

The aforementioned mixing bar 4 is supported slightly protruding from the bottom of the buffer member 6, and the protruding portion is engaged with the drive unit. This drive unit includes a drive motor 51 for applying rotation torque to the mixing bar 4 and gear sequence. A gear of the gear sequence is mounted at the end of the mixing bar 4 for transmitting the motor torque. It is worth noting that the gear sequence 52 may be other than the one depicted. A gear ratio is determined according to a particular necessity. Moreover, the output shaft of the drive motor 51 can be connected directly to the mixing bar 4.

Description will now be directed to operation of the liquid conveying catheter having the aforementioned configuration.

Firstly, the physiological saline solution M is discharged from the end of the supply tube 2 by being driven by the positive pressure pump 11 while the waste liquid S is sucked from the tip 31 of the collecting tube 3 driven by the negative pressure pump 12. Here, the collecting tube has on its inner wall, the coil-shaped member 32, which forms a helical groove 33. For suction, the waste S is urged by the mixing bar 4 rotated by the drive unit 5 so as to flow along the helical groove 33 inside the collecting tub.

Moreover, even if the collecting tube 3 is curved or cross section area decrease due to the inner pressure lowering, the mixing bar 4 is brought into abutment with the inner portion of the coil-shaped member 32, further deformation of the pipe can be prevented, while assuring a flow path in the helical groove 33. Thus, the waste liquid S continues to flow at a certain rate.

Accordingly, it is possible to collect the waste liquid S at a stable rate. With the aforementioned configuration, the collecting tube 3 can have a minimum cross sectional area.

Moreover, the helical convex in the collecting tube 3 is formed by the separate coil-member 32 from the collecting tube 3. This facilitates the production and increase the productivity.

Figure 3:
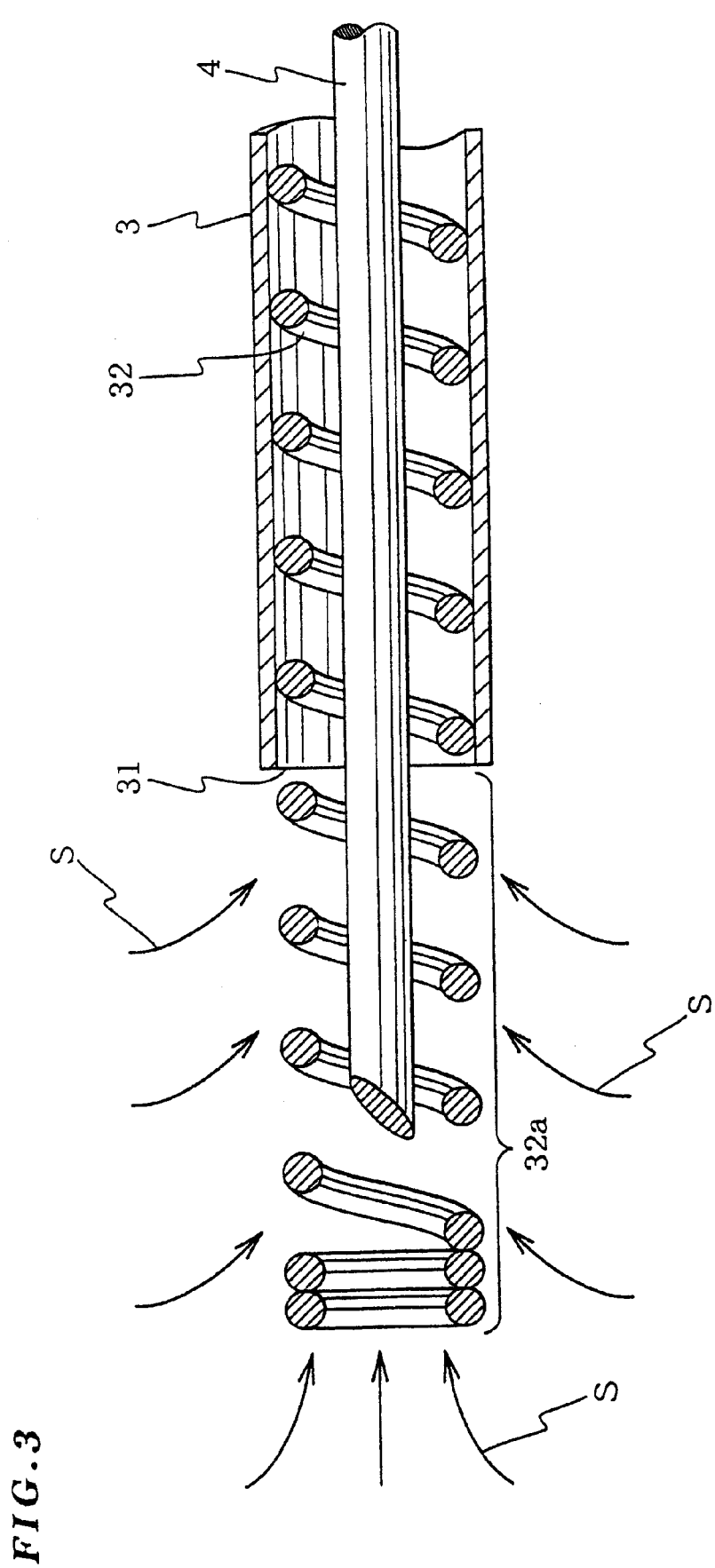
FIG. 3 shows a coil member of FIG. 1 mounted in a different way.

As shown in FIG. 3, the coil-shaped member 32 mounted in the collecting tube 32 may protrude from the insert tip 31 of the collecting tube 3. In this case, the mixing bar 4 extends to the vicinity of the tip of the coil-shaped member 32. Thus, when the coil-shaped member protrudes from the collecting tube 3, the protruding portion 32*a* serves as a filter. That is, a solid piece is stopped by the protrusion 32*a* and cannot be sucked inside the collecting pipe 3. This prevents clogging of the collecting tube 3 with such a solid piece.

Figure 4:
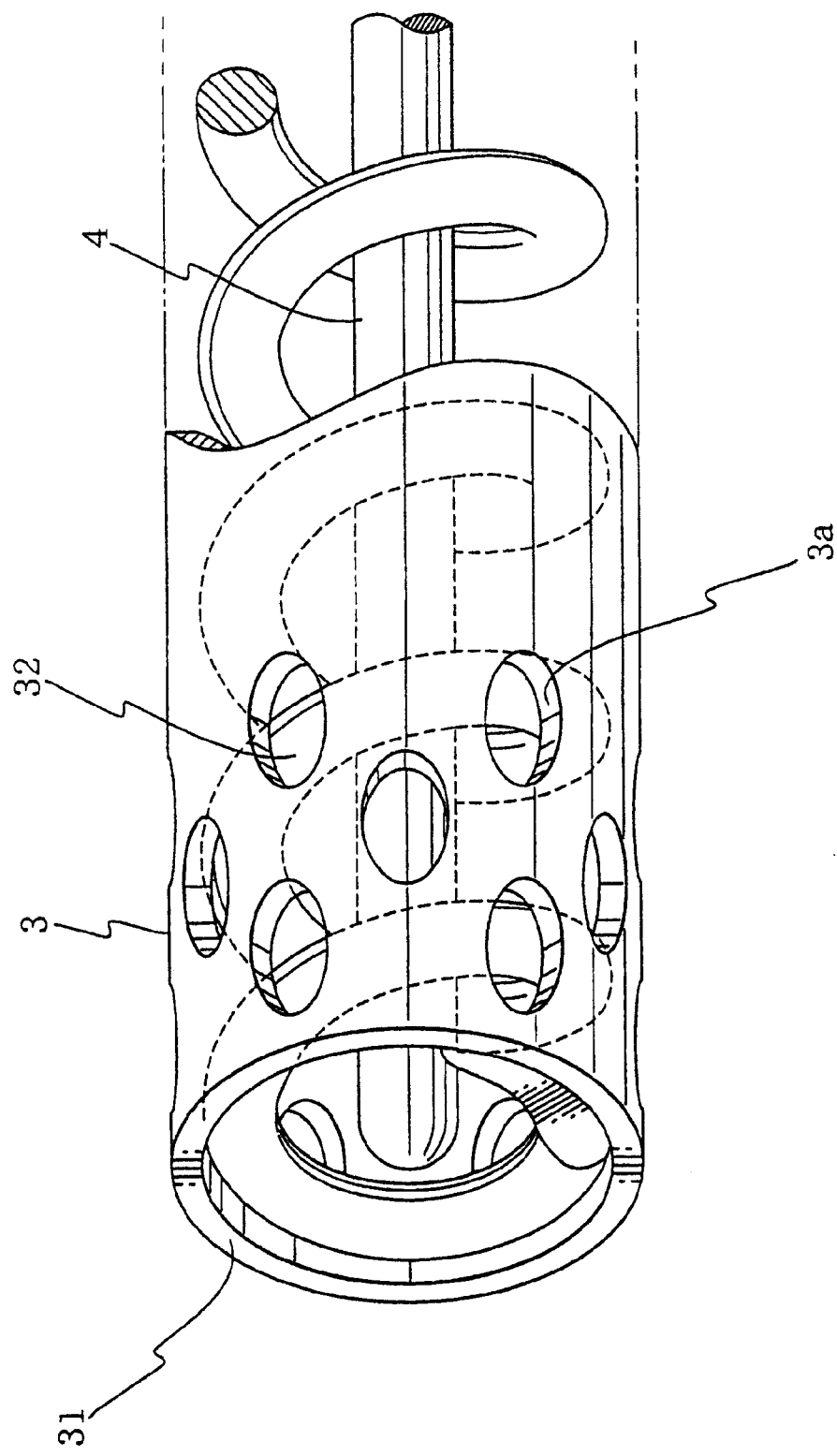
FIG. 4 is a perspective view of through holes provided in the collecting tube.

Moreover, as shown in FIG. 4, it is possible to form a number of through holes in the vicinity of the insert end 31 of the collecting tube 3. In this case also, a solid piece is stopped by the coil-shaped member 32, i.e., cannot be sucked into the collecting tube 3. Accordingly, like FIG. 3, it is possible to prevent sucking of a solid piece, thereby preventing clogging in the collecting tube 3.

Figure 5:
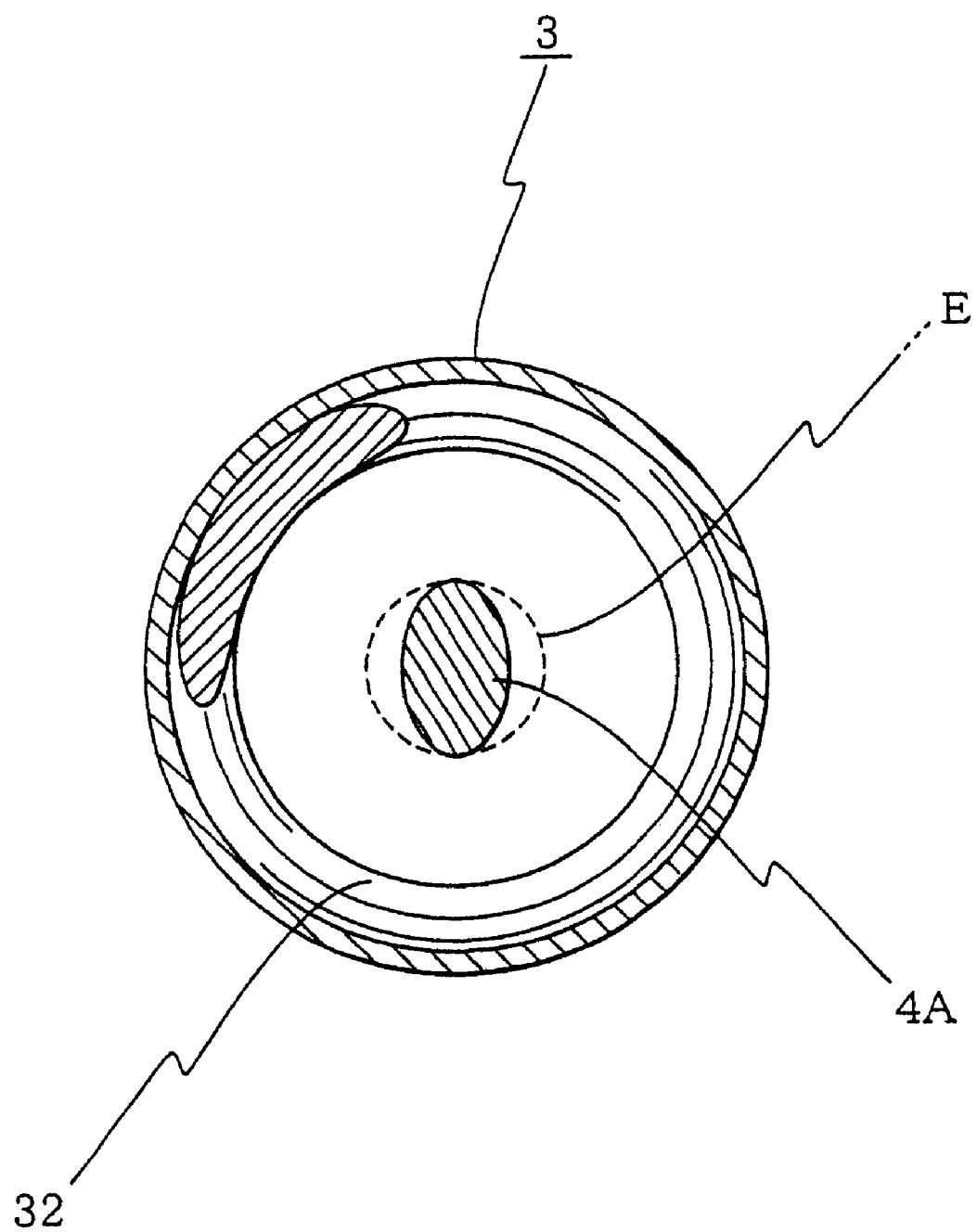
FIG. 5 is a cross sectional view of another example of a mixing bar in the collecting tube.

As for the mixing bar 4, its cross section may be other than circle. For example, as shown in FIG. 5, it is also possible to use a mixing bar 4A whose cross section may be an ellipse. In this case, the rotation radius of the mixing bar 4A directly urges the waste liquid S, increasing the flow rate.

Figure 6:
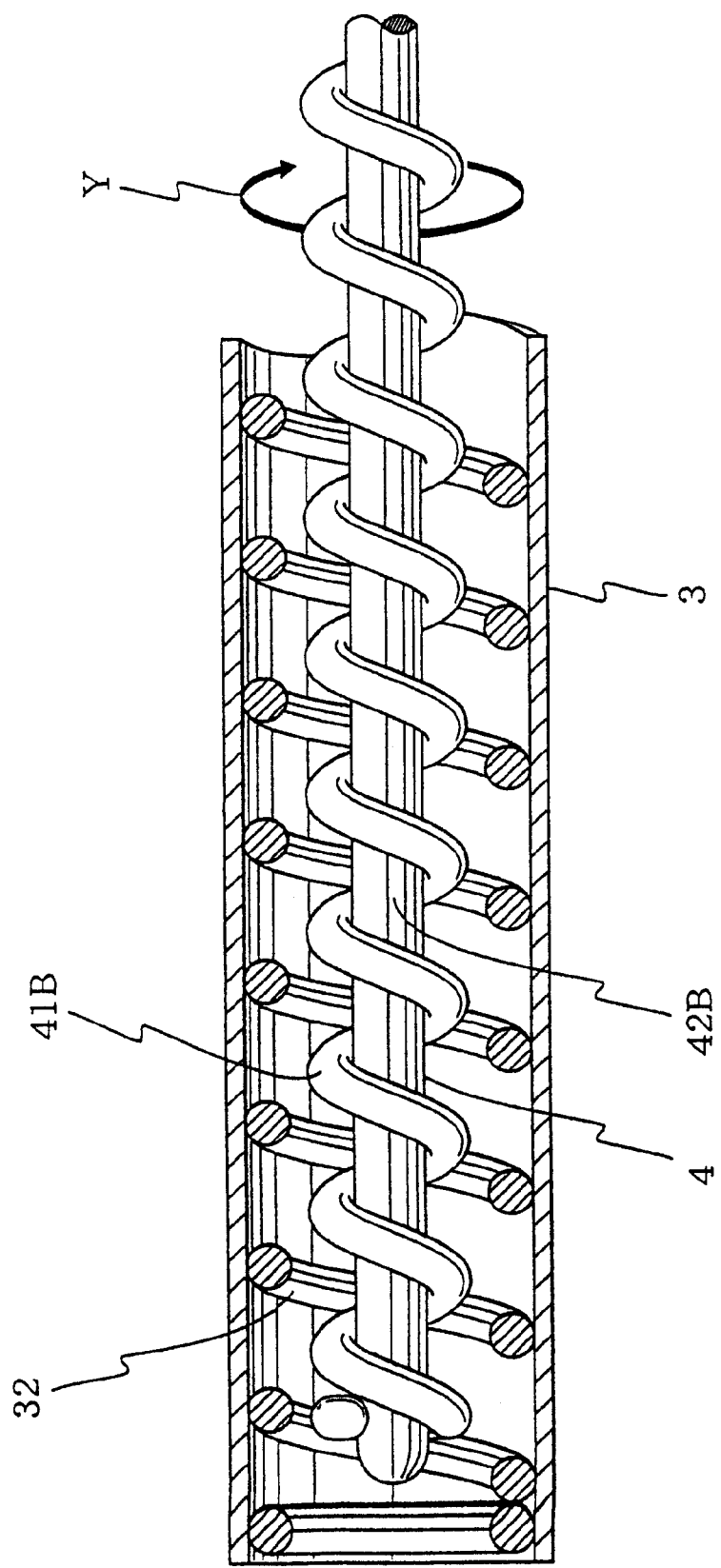
FIG. 6 is a cross sectional view of the collecting tube wherein the coil-shaped member is arranged on the mixing bar.

Moreover, as shown in FIG. 6, the aforementioned mixing bar 4 may have a helical convex around the center shaft. It is preferable that this helical convex be a coil-shaped member 41B formed separately from the mixing bar 4 and attached to the surface of the mixing bar 4 by melting. Here, the coil-shaped member 41B has an inner diameter identical to the outer diameter of the mixing bar 4 and an outer diameter smaller than the inner diameter of the coil-shaped member 32. Moreover, the rotation direction of the mixing bar 4, as indicated by Y, is preferably counterclockwise in this case, so that the waste liquid S flows in the suction direction. It should be noted that the winding direction of the coil-shaped member may be opposite (as in this figure) or identical to the coil-shaped member 32.

With this configuration, a helical groove 42B is formed by the coil-shaped member 41B on the outer circumferential surface of the mixing bar 4. Accordingly, even if the collecting tube 3 is curved or the cross sectional area is reduced by lowering the inner pressure, the helical groove 42 assures a flow path. Thus, the waste liquid S continues flowing with a high flow rate. Furthermore, the waste liquid S is also urged by the coil-shaped member 41B on the mixing bar 4. Thus, the waste liquid S is effectively flown.

As for the supply tube 2, it is possible to form a helical member on the inner wall of the supply tube and insert a mixing bar rotated by a drive unit. In this case, the rear end of the supply tube 2 is provided with a buffer member of the aforementioned configuration, and the supply tube is connected via a buffer member to the positive pressure pump 11.

With this configuration, a flow path of the physiological saline solution is assured, increasing a higher flow rate. Even if the supply pressure of the physiological saline solution is increased, it is possible to obtain a preferable flow.

Figure 7:
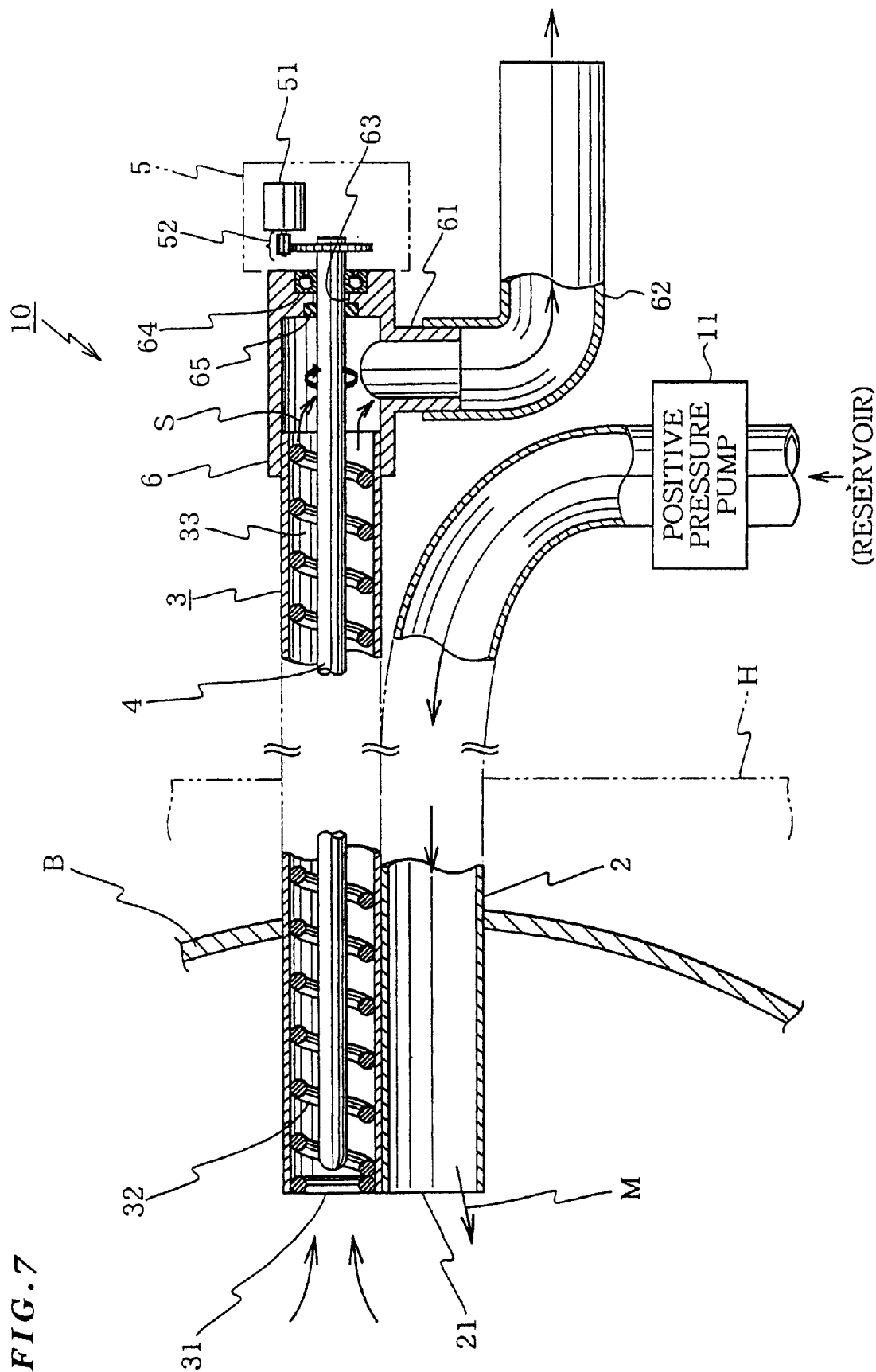
FIG. 7 shows a liquid carrying catheter capable of sucking a liquid using a mixing bar, a helical member, and drive unit.
Figure 8:
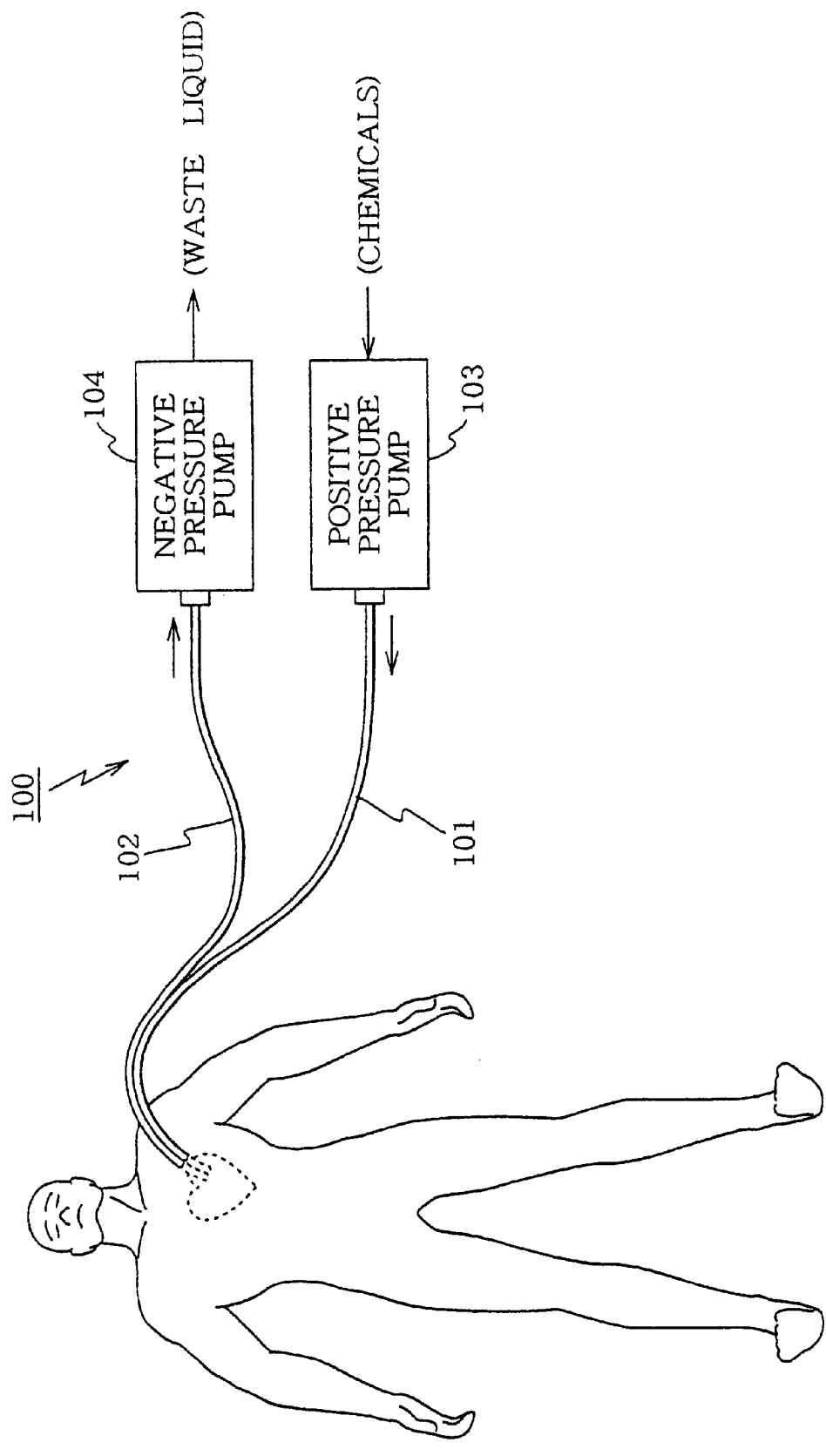
FIG. 8 shows a conventional catheter.

Furthermore, as shown in FIG. 7, the liquid carrying catheter 10 may not have any negative pressure pump at the end of the collecting pipe 3. That is, in the collecting pipe 3, the mixing bar 4 forms flow of the waste liquid S which flows along the groove defined by the coil-shaped member 32. The absence of the negative pressure pump has an advantage that contraction of the collecting pipe can be prevented, which in turn enables to obtain a preferable suction in a small-diameter tube having a large flow resistance.

As has been described above, the collecting tube has a helical convex on the inner wall of the collecting tube. This forms a helical groove facilitating flow of the waste liquid S. Moreover, a rotary mixing bar extends through the collecting tube. This enables to urge the waste liquid S along the helical groove effectively.

This configuration need not use of a suction pump. That is, a liquid can be sucked without setting a negative pressure in the collecting pipe. This is significantly advantageous especially in a small-diameter pipe.

Moreover, even if the collecting tube is curved or its cross sectional area is reduced by the inner pressure lowering, the mixing bar is brought into abutment with the helical convex, so that further deformation is prevented, thus assuring a helical groove for the flow path. That is, it is possible to maintain a constant flow rate. Accordingly, regardless of the negative pressure value, it is possible to collect a liquid at a constant flow rate. There is no danger of clogging, even if the tube diameter is decreased.

Since the helical convex in the collecting tube is a separate member attached to the inner wall of the collecting tube, this facilitates production and increases productivity.

According to another aspect of the present invention, the coil-shaped member protrudes from the insert end of the collecting pipe in the insert direction. Accordingly, this portion can serve as a filter for a solid body contained in the liquid to be sucked. This prevents clogging of the collecting tube.

According to yet another aspect of the present invention, the insert end portion of the collecting port has a number of through holes. This also serves as a filter and prevents clogging by a solid body contained in the liquid to be sucked.

According to still another aspect of the present invention, the mixing bar has an elliptical cross section for urging the liquid found in the rotation radius. This enables the liquid to effectively flow in the collecting pipe.

According to yet another aspect of the present invention, the mixing bar also has a helical convex, which defines a helical groove. Even if the collecting pipe is curved or the inner pressure is decreased to contract the cross section, the groove defined by the helical convex provided on the mixing bar assures a flow path inside the collecting pipe. Thus, it is possible to maintain a certain flow rate. Thanks to the helical groove on the rotating mixing bar, the liquid can effectively flow through the mixing pipe.

According to still yet another aspect of the present invention, the collecting pipe has a suction pump. As has been described above, the present invention assures a liquid flow path in the helical groove. Accordingly, even if a negative pressure is present in the collecting pipe, liquid suction can be assured.

The invention may be embodied in other specific forms without departing from the spirit or essential characteristic thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

The entire disclosure of Japanese Patent Application No. A10-309625 (Filed on Oct. 30, 1998) including specification, claims, drawings and summary are incorporated herein by reference in its entirety.

What is claimed is:

1. A liquid conveying catheter for conveying a liquid from an object from which the liquid is to be collected, the catheter comprising:
   a collecting tube having an insert end adapted to be inserted into the object for sucking a liquid;
   a mixing bar extending through the collecting tube and rotatably supported; and
   a drive unit for rotating the mixing bar,
   wherein the collecting tube has a helical convex on its inner wall around the center axis of the collecting tube, so as to define a helical groove serving as a flow path.

2. A liquid conveying catheter for supplying a liquid and collecting a liquid to/from an object, the catheter comprising:
   a supply tube having an insert end adapted to be inserted into the object for discharging the liquid;
   a collecting tube having an insert end adapted to be inserted into the object simultaneously with the supply tube, for sucking the liquid;
   a mixing bar extending through the collecting tube and rotatably arranged; and
   a drive unit for rotating the mixing bar,
   wherein the collecting tube has a helical convex on its inner wall around the center axis of the collecting tube, so as to define a helical groove, serving as a flow path.

3. A liquid conveying catheter as claimed in claim 1, wherein the helical convex is formed by a coil-shaped member fixed to the inner wall of the collecting tube.

4. A liquid conveying catheter as claimed in claim 2, wherein the helical convex is formed by a coil-shaped member fixed to the inner wall of the collecting tube.

5. A liquid conveying catheter as claimed in claim 3, wherein the coil-shaped member protrudes from the insert end of the collecting pipe in the insert direction.

6. A liquid conveying catheter as claimed in claim 4, wherein the coil-shaped member protrudes from the insert end of the collecting pipe in the insert direction.

7. A liquid conveying catheter as claimed in claim 1, wherein a plurality of through holes are provided at the insert end portion of the collecting tube.

8. A liquid conveying catheter as claimed in claim 2, wherein a plurality of through holes are provided at the insert end portion of the collecting tube.

9. A liquid conveying catheter as claimed in claim 3, wherein a plurality of through holes are provided at the insert end portion of the collecting tube.

10. A liquid conveying catheter as claimed in claim 4, wherein a plurality of through holes are provided at the insert end portion of the collecting tube.

11. A liquid conveying catheter as claimed in claim 1, wherein the mixing bar has an elliptical cross section.

12. A liquid conveying catheter as claimed in claim 2, wherein the mixing bar has an elliptical cross section.

13. A liquid conveying catheter as claimed in claim 3, wherein the mixing bar has an elliptical cross section.

14. A liquid conveying catheter as claimed in claim 4, wherein the mixing bar has an elliptical cross section.

15. A liquid conveying catheter as claimed in claim 1, wherein the mixing bar has a circular cross section and has a helical convex formed around the external surface of the mixing bar.

16. A liquid conveying catheter as claimed in claim 2, wherein the mixing bar has a circular cross section and has a helical convex formed around the external surface of the mixing bar.

17. A liquid conveying catheter as claimed in claim 3, wherein the mixing bar has a circular cross section and has a helical convex formed around the external surface of the mixing bar.

18. A liquid conveying catheter as claimed in claim 4, wherein the mixing bar has a circular cross section and has a helical convex formed around the external surface of the mixing bar.

19. A liquid conveying catheter as claimed in claim 2, wherein the supply tube has: a helical convex on its inner wall around the center axis of the supply tube, so as to define a helical groove; and a mixing bar extending through the supply tube and rotatably supported and provided with a drive unit for rotating the mixing bar.

20. A liquid conveying catheter as claimed in one of the foregoing Claims, wherein a suction pump is provided at the insert end and opposite end of the collecting tube.

* * * * *